(12) United States Patent
Schade et al.

(10) Patent No.: US 9,808,410 B2
(45) Date of Patent: Nov. 7, 2017

(54) OCTOCRYLENE-FREE SUNSCREEN COMPOSITION WITH LOW STICKINESS

(71) Applicant: Beiersdorf AG, Hamburg (DE)

(72) Inventors: Tatjana Schade, Mildstedt/Rosendahl (DE); Kerstin Skubsch, Prisdorf (DE); Sina Brinkmann, Kalbe (DE); Andreas Bleckmann, Ahrensburg (DE); David Schlenker, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 278 days.

(21) Appl. No.: 14/603,702

(22) Filed: Jan. 23, 2015

(65) Prior Publication Data

US 2015/0209259 A1 Jul. 30, 2015

(30) Foreign Application Priority Data

Jan. 29, 2014 (DE) .................. 10 2014 201 541

(51) Int. Cl.
| | | |
|---|---|---|
| *A61K 8/18* | (2006.01) | |
| *A61K 8/49* | (2006.01) | |
| *A61K 8/06* | (2006.01) | |
| *A61K 8/35* | (2006.01) | |
| *A61Q 17/04* | (2006.01) | |
| *A61K 8/34* | (2006.01) | |

(52) U.S. Cl.
CPC ............ *A61K 8/4966* (2013.01); *A61K 8/062* (2013.01); *A61K 8/345* (2013.01); *A61K 8/35* (2013.01); *A61K 8/4946* (2013.01); *A61Q 17/04* (2013.01); *A61K 2800/30* (2013.01)

(58) Field of Classification Search
CPC .......... A61K 2800/48; A61K 2800/522; A61K 47/22; A61K 8/025; A61K 8/0279; A61K 8/466; A61K 8/585; A61K 8/731; A61K 8/894; A61K 47/14
See application file for complete search history.

(56) References Cited

U.S. PATENT DOCUMENTS

| | | | | |
|---|---|---|---|---|
| 2004/0028709 A1* | 2/2004 | Dueva | ...................... | A61K 8/73 424/401 |
| 2009/0016971 A1 | 1/2009 | Gaudry et al. | | |
| 2011/0014139 A1* | 1/2011 | Viala | ...................... | A61Q 17/04 424/59 |
| 2011/0081304 A1* | 4/2011 | Garay | ...................... | A61K 8/97 424/59 |
| 2013/0344015 A1 | 12/2013 | Gaudry et al. | | |

FOREIGN PATENT DOCUMENTS

| | | |
|---|---|---|
| DE | 19846771 A1 | 4/2000 |
| DE | 102012200074 A1 | 7/2013 |

* cited by examiner

*Primary Examiner* — Nannette Holloman
(74) *Attorney, Agent, or Firm* — Abel Law Group, LLP

(57) ABSTRACT

Disclosed is a cosmetic sunscreen composition comprising a UV filter combination of
a) 4-(tert-butyl)-4'-methoxydibenzoylmethane,
b) 2,4,6-tris[anilino(p-carbo-2'-ethyl-1'-hexyloxy)]-1,3,5-triazine (INCI: Ethylhexyl Triazone),
c) 2,4-bis{[4-(2-ethylhexyloxy)-2-hydroxy]phenyl}-6-(4-methoxyphenyl)-1,3,5-triazine (INCI: Bis-Ethylhexyloxyphenol methoxyphenyl Triazine),
d) 2-phenylbenzimidazole-5-sulfonic acid and/or one or more salts thereof.

20 Claims, 1 Drawing Sheet

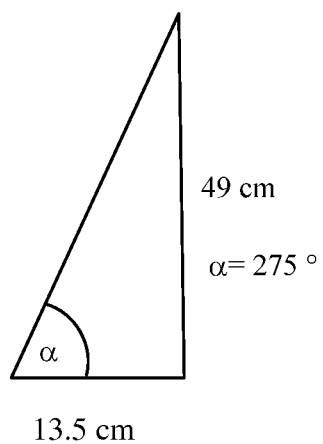

OCTOCRYLENE-FREE SUNSCREEN COMPOSITION WITH LOW STICKINESS

CROSS-REFERENCE TO RELATED APPLICATIONS

The present application claims priority under 35 U.S.C. §119 of German Patent Application No. 10 2014 201 541.3, filed Jan. 29, 2014, the entire disclosure of which is expressly incorporated by reference herein.

BACKGROUND OF THE INVENTION

1. Field of the Invention

The present invention relates to a cosmetic preparation comprising a UV filter combination of 4-(tert-butyl)-4'-methoxydibenzoylmethane, 2,4,6-tris[anilino(p-carbo-2'-ethyl-1'-hexyloxy)]-1,3,5-triazine (INCI: Ethylhexyl Triazone), 2,4-bis{[4-(2-ethylhexyloxy)-2-hydroxy]phenyl}-6-(4-methoxyphenyl)-1,3,5-triazine (INCI: Bis-Ethylhexyloxyphenol methoxyphenyl Triazine), and 2-phenylbenzimidazole-5-sulfonic acid and/or one or more salts thereof.

2. Discussion of Background Information

The trend away from a gentile pallor toward "healthy, sportly brown skin" has been unbroken for years. In order to achieve this, people expose their skin to solar radiation, since this brings about pigment formation in the sense of melanin formation. However, the ultraviolet radiation in sunlight also has a damaging effect on the skin. Besides the acute damage (sunburn), there is long-term damage such as an increased risk of suffering from skin cancer on excessive irradiation with light from the UVB range (wavelength: 280-320 nm). Moreover, the effect of too much UVB and UVA radiation (wavelength: 320-400 nm) is a weakening of the elastic and collagenous fibers of the connective tissue. This leads to numerous phototoxic and photoallergic reactions, resulting in premature skin aging.

In order to protect the skin, therefore, a range of photoprotective filter substances have been developed that can be used in cosmetic preparations. In the majority of industrialized countries, these UVA and UVB filters are collated in the form of positive lists such as Annex 7 of the German Cosmetics Ordinance.

The multiplicity of commercially available sunscreen compositions should not, however, distract from the fact that these prior-art preparations have a range of disadvantages.

Because of factors including their UV filter content, cosmetic sunscreen compositions usually have a certain stickiness, which particularly in beach use means that sand ends up adhering to parts of the skin to which cream has been applied. The greater the UV filter content of a preparation, the greater this problem. While in the past there has been no lack of attempts to develop sand-repellent sunscreen compositions, this problem has nevertheless to date not been solved to ultimate satisfaction, particularly in the case of preparations featuring a high sun protection factor.

It would thus be advantageous to have available a sand-repellent sunscreen composition, more particularly a sunscreen composition having a high sun protection factor (SPF 50 or more) that exhibits particularly low sand adhesion.

In addition to the stickiness/sand adhesion, moreover, a problem of cosmetic sunscreen compositions is that very many UV filters do not have particularly good solubility in the preparations. Especially if preparations with a high sun protection factor and high UV filter content are developed, the developers face the problem of the solubility of triazine derivatives and 4-(tert-butyl)-4'-methoxydibenzoylmethane. In the past, in order to solve this problem, the liquid UV-B filter octocrylene has been used as UV filter and solvent.

A further disadvantage of the prior art lies in the circumstance that a range of further ingredients in sunscreen compositions are unstable to light and/or are destroyed or undergo volatilization under thermal exposure. The photoinstability of the UV-A filter and 4-(tert-butyl)-4'-methoxydibenzoylmethane poses a particular challenge in this context. Octocrylene, preferably, is likewise used according to the prior art for the photostabilization of 4-(tert-butyl)-4'-methoxydibenzoylmethane.

The disadvantage of the prior art lies, then, in the circumstance that the use of octocrylene, in spite of its approval by the approval authorities, is not entirely uncontroversial and results, when evaluations are undertaken in certain consumer magazines (e.g., the German Öko-test), in "markdowns" in the scoring of the product. The reason given for this negative evaluation is that certain scientists suspect that this UV filter might possibly have hormonal activity. Even when no negative effects in people have become apparent in spite of the decades-long use of this UV filter worldwide in sunscreen compositions, there is still a desire among consumers to avoid preparations containing such ingredients.

It, therefore is desirable to overcome the disadvantages of the prior art and to develop a sand-repellent sunscreen composition with a high sun protection factor, in which the UV filters are stably dissolved and the photochemical degradation of 4-(tert-butyl)-4'-methoxydibenzoylmethane is suppressed. Ideally it ought to be possible to achieve the object without using octocrylene as solvent and stabilizer.

SUMMARY OF THE INVENTION

The present invention provides a cosmetic sunscreen composition. The composition comprises a UV filter combination of
  a) 4-(tert-butyl)-4'-methoxydibenzoylmethane,
  b) 2,4,6-tris[anilino(p-carbo-2'-ethyl-1'-hexyloxy)]-1,3,5-triazine (INCI: Ethylhexyl Triazone),
  c) 2,4-bis{[4-(2-ethylhexyloxy)-2-hydroxy]phenyl}-6-(4-methoxyphenyl)-1,3,5-triazine (INCI: Bis-Ethylhexyloxyphenol methoxyphenyl Triazine), and
  d) 2-phenylbenzimidazole-5-sulfonic acid and/or one or more salts thereof.

In one aspect of the composition, the composition may contain no 3-(4-methylbenzylidene)-camphor, 2-hydroxy-4-methoxybenzophenone (INCI: Oxybenzone), and ethylhexyl 2-cyano-3,3-diphenylacrylate (INCI: Octocrylene) and/or may contain no titanium dioxide and zinc oxide.

In another aspect, the composition may be present as an emulsion, in particular an O/W emulsion.

In yet another aspect, the composition may comprise sodium stearylglutamate as emulsifier and/or Silica Dimethyl Silylate and/or one or more of dibutyl adipate, dicaprylyl carbonate, C12-C15 alkylbenzoate.

In a still further aspect, the composition of the present invention may comprise one or more of alpha-lipoic acid, folic acid, phytoene, D-biotin, coenzyme Q10, alpha-glucosylrutin, carnitin, carnosin, natural and/or synthetic isoflavonoids, flavonoids, creatine, creatinine, taurine, β-alanine, tocopheryl acetate, dihydroxyacetone; 8-hexadecene-1,16-dicarboxylic acid, glycerylglycose, (2-hydroxyethyl)urea, vitamin E and/or derivatives thereof, hyaluronic acid and/or salts thereof, licochalcone A.

In another aspect, the composition may comprise one or more of 1,2-pentanediol, 1,2-hexanediol, 1,2-octanediol, 1,2-decanediol, 2-methyl-1,3-propanediol and/or may comprise one or more of ethanol, phenoxyethanol, ethylhexylglycerol and/or may comprise one or more of xanthan gum, crosslinked acrylate/C10-C30 alkyl acrylate polymer, vinylpyrrolidone/hexadecene copolymer and/or may comprise one or more of cetyl alcohol, stearyl alcohol, glyceryl stearate.

In another aspect, the composition may be free from parabens, methylisothiazolinone, chloromethylisothiazolinone, DMDM-hydantoin.

In another aspect, the composition may comprise one or more fragrances selected from limonene, citral, linalool, alpha-isomethylionone, geraniol, citronellol, 2-isobutyl-4-hydroxy-4-methyltetrahydropyran, 2-tert-pentylcyclohexyl acetate, 3-methyl-5-phenyl-1-pentanol, 7-acetyl-1,1,3,4,4,6-hexamethyltetralin, adipic diester, alpha-amylcinnamaldehyde, alpha-methylionone, amyl C butylphenylmethylpropional cinnamal, amyl salicylate, amylcinnamyl alcohol, anise alcohol, benzoin, benzyl alcohol, benzyl benzoate, benzyl cinnamate, benzyl salicylate, bergamot oil, bitter orange oil, butylphenylmethylpropional, cardamom oil, cedrol, cinnamal, cinnamyl alcohol, citronellyl methylcrotonate, citrus oil, coumarin, diethyl succinate, ethyllinalool, eugenol, *Evernia furfuracea* extract, *Evernia prunastri* extract, farnesol, guaiacwood oil, hexylcinnamal, hexyl salicylate, hydroxycitronellal, lavender oil, lemon oil, linalyl acetate, mandarin oil, menthyl PCA, methyl heptenone, nutmeg oil, rosemary oil, sweet orange oil, terpineol, tonkabean oil, triethyl citrate, vanillin.

In another aspect, the composition may contain at least one salt of 2-phenylbenzimidazole-5-sulfonic acid.

In another aspect, the composition may have an SPF of at least 50.

BRIEF DESCRIPTION OF THE DRAWING

In the accompanying drawing, the only FIGURE shows the construction of the slide apparatus used in the Examples below.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description in combination with the drawing making apparent to those skilled in the art how the several forms of the present invention may be embodied in practice.

It is preferred in accordance with the invention if the preparation contains no 3-(4-methylbenzylidene)camphor, 2-hydroxy-4-methoxybenzophenone (INCI: Oxybenzone), and ethylhexyl 2-cyano-3,3-diphenylacrylate (INCI: Octocrylene), therefore being free of these ingredients.

It is advantageous in accordance with the invention if the preparation of the invention contains no titanium dioxide and zinc oxide.

The preparations of the invention manage with a surprisingly small total amount of UV filters.

In addition to the UV filter combination claimed, the preparation of the invention may comprise one or more further UV filters. These may be selected, advantageously in accordance with the invention, from phenylene-1,4-bis(2-benzimidazyl)-3,3',5,5'-tetrasulfonic acid salts; 1,4-di(2-oxo-10-sulfo-3-bornylidenemethyl)benzene and its salts; 4-(2-oxo-3-bornylidenemethyl)-benzenesulfonic acid salts; 2-methyl-5-(2-oxo-3-bornylidenemethyl)sulfonic acid salts; 2,2'-me-thylenebis(6-(2H-benzotriazol-2-yl)-4-(1,1,3,3-tetramethylbutyl)phenol); 2-(2H-benzotriazol-2-yl)-4-methyl-6-[2-methyl-3-[1,3,3,3-tetramethyl-1-[(trimethylsilyl)oxy]disiloxanyl]propyl]-phenol; 3-benzylidenecamphor; terephthalidenedicamphorsulfonic acid; 2-ethylhexyl 4-(dimethylamino)benzoate; amyl 4-(dimethylamino)benzoate; di(2-ethylhexyl) 4-methoxybenzalmalonate; isoamyl 4-methoxycinnamoate; hexyl 2-(4'-diethylamino-2'-hydroxybenzoyl)benzoate, ethylhexyl salicylate, homomenthyl salicylate, 2-ethylhexyl 2-hydroxybenzoate; dimethicodiethyl benzalmalonate; 3-(4-(2,2-bis-ethoxycarbonylvinyl)-phenoxy)propenyl)methoxysiloxane/dimethylsiloxane copolymer; dioctylbutylamidotriazone (INCI: Diethylhexyl-Butamidotriazone); 2,4,6-tribiphenyl-4-yl-1,3,5-triazine.

It is advantageous in accordance with the invention if the preparation is present in the form of an emulsion or dispersion, preferably in the form of an emulsion, and more preferably in the form of an O/W emulsion.

Where the preparation of the invention is in the form of an O/W emulsion, the preparation advantageously comprises one or more O/W emulsifiers selected from glyceryl stearate citrate, glyceryl stearate (self-emulsifying), stearic acid, stearate salts, polyglyceryl-3-methylglycose distearate, sodium cetearylsulfate, potassium cetylphosphate, polyglyceryl-10 stearate, and sodium stearylglutamate.

Advantageously in accordance with the invention, these O/W emulsifiers of the invention may be present in the preparation in a concentration of 0.001 to 10 wt % and preferably in a concentration of 0.1 to 7 wt %, based on the total weight of the preparation.

It is preferred in accordance with the invention if the preparation comprises sodium stearylglutamate as emulsifier.

It is further advantageous in accordance with the invention if the preparation comprises cetyl alcohol, stearyl alcohol and/or glycerylstearate.

It is of advantage in accordance with the invention if the preparation of the invention is free from polyethylene glycol, polyethylene glycol ethers, and polyethylene glycol esters (so-called PEG derivatives).

The preparation of the invention may advantageously comprise moisturizers. Moisturizers are compounds or mixtures of compounds which give cosmetic preparations the quality, after application to or distribution on the skin surface, of reducing the loss of moisture of the stratum corneum (also called transepidermal water loss (TEWL)) and/or of positively influencing the hydration of the stratum corneum.

Non-limiting examples of advantageous moisturizers for use in the present invention include glycerol, lactic acid and/or lactates, especially sodium lactate, butylene glycol, propylene glycol, biosaccharide gum-1, Glycine soya, ethylhexyloxyglycerol, pyrrolidonecarboxylic acid, and urea. Of further advantage, in particular, is the use of polymeric moisturizers from the group of the polysaccharides which are water-soluble and/or swellable in water and/or gellable with the aid of water. Especially advantageous, for example, are hyaluronic acid, chitosan and/or a fucose-rich polysaccharide which is registered in Chemical Abstracts under the registry number 178463-23-5 and is available, for example, under the Fucogel®1000 name from the company SOLABIA S.A. Moisturizers may also be used advantageously as active antiwrinkle ingredients for protection from changes to the skin of the kind occurring in skin aging, for example.

The cosmetic preparations of the invention may further comprise advantageously, although not mandatorily, fillers which have the effect, for example, of further improving the sensorial and cosmetic properties of the formulations and evoking or intensifying a velvety or silky skin sensation, for example. Advantageous fillers in the sense of the present invention are starch and starch derivatives (such as tapioca starch, distarch phosphate, aluminum or sodium starch octenylsuccinate, and the like, for example), pigments which have neither primarily UV filter effect nor coloring effect (such as boron nitride, etc., for example) and/or Aerosils® (CAS No. 7631-86-9) and/or talc and/or polyethylene, nylon, and silica dimethyl silylate.

It is preferred in accordance with the invention if the preparation of the invention comprises silica dimethyl silylate.

Advantageous embodiments of the preparation of the present invention also include those wherein the preparation comprises one or more oils selected from butylene glycol dicaprylate/dicaprate, phenethyl benzoate, C12-15 alkyl benzoate, dibutyl adipate; diisopropyl sebacates, dicaprylyl carbonate, di-C12-13 alkyl tartrates, butyloctyl salicylates, diethylhexyl syringylidene malonates, hydrogenated castor oil dimerates, triheptanoin, C12-13 alkyl lactates, C16-17 alkyl benzoates, propylheptyl caprylates, caprylic/capric triglycerides, diethylhexyl 2,6-naphthalates, octyldodecanol, ethylhexyl cocoates.

It is preferred in accordance with the invention if the preparation comprises dibutyl adipate, dicaprylyl carbonate and/or C12-C15 alkyl benzoate.

The water phase of the preparations of the invention may advantageously comprise customary cosmetic auxiliaries, such as, for example, alcohols, particularly those of low C number, preferably ethanol and/or isopropanol, or polyols of low C number, and also ethers thereof, preferably propylene glycol, glycerol, electrolytes, self-tanning agents, and also, in particular, one or more thickeners, which may be advantageously selected from the group of silicon dioxide, aluminum silicates, polysaccharides and/or derivatives thereof, e.g., hyaluronic acid, xanthan gum, hydroxypropylmethylcellulose, particularly advantageously from the group of polyacrylates, preferably a polyacrylate from the group referred to as Carbopols, examples being carbopols of types 980, 981, 1382, 2984, and 5984, in each case individually or in combination. Further thickeners advantageous in accordance with the invention are those having the INCI designation Acrylates/C10-30 Alkyl Acrylate Crosspolymer (e.g., Pemulen TR 1, Pemulen TR 2, Carbopol 1328 from NOVEON) and also Aristoflex AVC (INCI: Ammonium Acryloyldimethyltaurate/VP Copolymer).

It is preferred here in accordance with the invention if the preparation comprises xanthan gum, crosslinked acrylate/C10-C30 alkyl acrylate polymer, and/or vinylpyrrolidone/hexadecene copolymer.

An amount of glycerol of at least 5 wt %, based on the total weight of the preparation, is particularly advantageous in accordance with the invention.

Embodiments of the present invention that are advantageous in accordance with the invention are those wherein the preparation comprises one or more compounds selected from alpha-lipoic acid, folic acid, phytoene, D-biotin, coenzyme Q10, alpha-glucosylrutin, carnitin, carnosin, natural and/or synthetic isoflavonoids, flavonoids, creatine, creatinine, taurine, β-alanine, tocopheryl acetate, dihydroxyacetone; 8-hexadecene-1,16-dicarboxylic acid, glycerylglycose, (2-hydroxy-ethyl)urea, vitamin E and/or derivatives thereof, hyaluronic acid and/or salts thereof, licochalcone A.

It is advantageous in accordance with the invention if the preparation comprises one or more alkanediols from the group 1,2-pentanediol, 1,2-hexanediol, 1,2-octanediol, 1,2-decanediol, 2-methyl-1,3-propanediol.

It is advantageous in accordance with the invention if the preparation of the invention comprises ethanol, phenoxyethanol and/or ethylhexylglycerol.

Embodiments of the present invention that are advantageous in accordance with the invention also include those wherein the preparation is free from parabens, methylisothiazolinone, chloromethylisothiazolinone, and DMDM-hydantoin.

It is further advantageous in the sense of the present invention if the preparation of the invention comprises one or more fragrances selected from limonene, citral, linalool, alpha-isomethylionone, geraniol, citronellol, 2-isobutyl-4-hydroxy-4-methyltetrahydropyran, 2-tert-pentylcyclohexyl acetate, 3-methyl-5-phenyl-1-pentanol, 7-acetyl-1,1,3,4,4,6-hexamethyltetralin, adipic diester, alpha-amylcinnamaldehyde, alpha-methylionone, amyl C butylphenylmethylpropional cinnamal, amyl salicylate, amylcinnamyl alcohol, anise alcohol, benzoin, benzyl alcohol, benzyl benzoate, benzyl cinnamate, benzyl salicylate, bergamot oil, bitter orange oil, butylphenylmethylpropional, cardamom oil, cedrol, cinnamal, cinnamyl alcohol, citronellyl methylcrotonate, citrus oil, coumarin, diethyl succinate, ethyllinalool, eugenol, *Evernia furfuracea* extract, *Evernia prunastri* extract, farnesol, guaiacwood oil, hexylcinnamal, hexyl salicylate, hydroxycitronellal, lavender oil, lemon oil, linalyl acetate, mandarin oil, menthyl PCA, methyl heptenone, nutmeg oil, rosemary oil, sweet orange oil, terpineol, tonkabean oil, triethyl citrate, vanillin.

Advantageously in accordance with the invention, the preparation of the invention comprises film formers. Film formers in the sense of the present invention are substances of various constitutions, and are characterized by the following properties: When a film former is dissolved in water or other suitable solvents, and when the solution is then applied to the skin, the film former, following evaporation of the solvent, forms a film which serves essentially to fix the photofilters on the skin and to so increase the water resistance of the product.

It is especially advantageous to select the film formers from the group of the polymers based on polyvinylpyrrolidone (PVP)

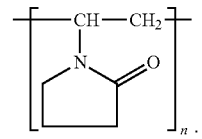

Particular preference is given to copolymers of vinylpyrrolidone, as for example the PVP hexadecene copolymer and the PVP eicosene copolymer, which are available under the trade names Antaron V216 and Antaron V220 from GAF Chemicals Corporation.

Likewise advantageous are further polymeric film formers, such as, for example, sodium polystyrene sulfonate, which is available under the trade name Flexan 130 from National Starch and Chemical Corp., and/or polyisobutene, available from Rewo under the trade name Rewopal PIB1000. Examples of further suitable polymers are polyacrylamides (Seppigel 305), polyvinyl alcohols, PVP, PVP/VA copolymers, polyglycols, acrylate/octylacrylamide copolymer (Dermacryl 79) Likewise advantageous is the use of hydrogenated castor oil dimer dilinoleate (CAS 646054-62-8, INCI Hydrogenated Castor Oil Dimer Dilinoleate), which can be acquired from Kokyu Alcohol Kogyo under the name Risocast DA-H, or else PPG-3 benzyl ether myristate (CAS 403517-45-3), which can be acquired under trade name Crodamol STS from Croda Chemicals.

In accordance with the invention is the use of the preparation of the invention for protection from skin aging (especially for protection from UV-induced skin aging) and also as a sun protection composition.

In accordance with the invention is also the use of the UV filter combination of the invention for reducing sand adhesion in cosmetic preparations (especially sunscreen compositions). In accordance with the invention in particular in this case is the use of salts of 2-phenyl-benzimidazol-5-sulfonic acid, and also the use of 2,4,6-tris[anilino(p-carbo-2'-ethyl-F-hexyl-oxy)]-1,3,5-triazine (INCI: Ethylhexyl Triazone), for reducing the sand adhesion in cosmetic preparations (especially sunscreen compositions).

COMPARATIVE EXPERIMENT/EXAMPLE FORMULA

The following formulas were produced and the sand adhesion was determined using the method below. Formula 1 here is an inventive embodiment:

| Formula comparison | | | |
|---|---|---|---|
| INCI | Formula 1 m [g] | Formula 2 m [g] | Formula 3 m [g] |
| Glyceryl Stearate | 1.00 | 1.00 | 1.00 |
| Water | 52.72 | 54.02 | 55.72 |
| Dibutyl Adipate | 3.00 | 3.00 | 3.00 |
| Cetearyl Alcohol | 1.00 | 1.00 | 1.00 |
| Trisodium EDTA | 1.00 | 1.00 | 1.00 |
| C12-15 Alkyl Benzoate | 6.00 | 6.00 | 6.00 |
| Butyl Methoxydibenzoylmethane | 4.50 | 4.50 | 4.50 |
| Phenylbenzimidazole Sulfonic Acid | 1.00 | | 1.00 |
| VP/Hexadecene Copolymer | 0.50 | 0.50 | 0.50 |
| Glycerin + Water | 7.50 | 7.50 | 7.50 |
| Water + Sodium Hydroxide | 0.38 | 0.08 | 0.38 |
| Alcohol Denat. + Water | 4.00 | 4.00 | 4.00 |
| Xanthan Gum | 0.40 | 0.40 | 0.40 |
| Ethylhexyl Triazone | 3.00 | 3.00 | |
| Acrylates/C10-30 Alkyl Acrylate Crosspolymer | 0.10 | 0.10 | 0.10 |
| Silica Dimethyl Silylate | 0.50 | 0.50 | 0.50 |
| Ethylhexylglycerin | 0.50 | 0.50 | 0.50 |
| C18-38 Alkyl Hydroxystearoyl Stearate | 1.00 | 1.00 | 1.00 |
| Bis-Ethylhexyloxyphenol Methoxyphenyl Triazine | 3.50 | 3.50 | 3.50 |
| Butylene Glycol Dicaprylate/Dicaprate | 5.00 | 5.00 | 5.00 |
| Methylpropanediol | 3.00 | 3.00 | 3.00 |
| Sodium Stearoyl Glutamate | 0.40 | 0.40 | 0.40 |
| Total | 100.00 | 100.00 | 100.00 |

In Vitro Sand Adhesion 50 mg of the test emulsion was applied to PMMA Schönberg plaques (5.0×5.0 cm) and spread uniformly over the plaque, using a fingerstall. The example formula applied is then dried at room temperature for 15 minutes. After this time, the weight of the dried plaques is determined using an analytical balance. After that the plaques are sprinkled with fine marine sand (1.07711.1000 Seesand reinst, from Merck KGaA) in excess. Loose adhering sand was removed with a reproducible, unitary force, by causing the plaques to slide once on a slide apparatus intended for that purpose (see below).

The adhering sand remaining on the plaque thereafter was determined by reweighing. The sand adhesion can be determined using the following equation:

$$\Delta(\text{Adhesion})[mg] = m(\text{plaque with sand})[mg] - m(\text{plaque with cream applied})[mg]$$

The slide apparatus is a construction in the form of a triangle on which the width of the slide is 5 cm. The construction of the slide apparatus is apparent in more detail from the drawing.

The experiments were repeated 10× per formula and the corresponding mean was formed.

| Formula 1 | | | | |
|---|---|---|---|---|
| Plaque with emulsion | Plaque with sand | Sand (adhering) | Mean | Standard deviation |
| 7.312 | 7.702 | 0.39 | | |
| 7.3 | 7.663 | 0.363 | | |
| 7.306 | 7.781 | 0.475 | | |
| 7.298 | 7.744 | 0.446 | | |
| 7.307 | 7.763 | 0.456 | | |
| 7.288 | 7.693 | 0.405 | | |
| 7.307 | 7.619 | 0.312 | | |
| 7.305 | 7.735 | 0.43 | | |
| 7.317 | 7.744 | 0.427 | | |
| 7.31 | 7.727 | 0.417 | 0.412 | 0.048 |

Since the plaque is 25 cm$^2$ in size: 16.48 mg/cm$^2$ for 1.92 standard deviation

| Formula 2 | | | | |
|---|---|---|---|---|
| Plaque with emulsion | Plaque with sand | Sand (adhering) | Mean | Standard deviation |
| 7.312 | 7.826 | 0.514 | | |
| 7.302 | 7.76 | 0.48 | | |
| 7.317 | 7.793 | 0.476 | | |
| 7.299 | 7.669 | 0.37 | | |
| 7.322 | 7.622 | 0.3 | | |
| 7.294 | 7.75 | 0.456 | | |
| 7.308 | 7.749 | 0.441 | | |
| 7.307 | 7.725 | 0.418 | | |
| 7.321 | 7.666 | 0.345 | | |
| 7.3 | 7.7 | 0.4 | 0.42 | 0.067 |

Since the plaque is 25 cm$^2$ in size: 16.80 mg/cm$^2$ for 2.68 standard deviation

| Formula 3 | | | | |
|---|---|---|---|---|
| Plaque with emulsion | Plaque with sand | Sand (adhering) | Mean | Standard deviation |
| 7.301 | 7.701 | 0.4 | | |
| 7.32 | 7.72 | 0.4 | | |
| 7.323 | 7.773 | 0.45 | | |
| 7.302 | 7.702 | 0.4 | | |
| 7.296 | 7.716 | 0.42 | | |
| 7.307 | 7.887 | 0.58 | | |
| 7.318 | 7.742 | 0.424 | | |
| 7.31 | 7.72 | 0.41 | | |
| 7.309 | 7.849 | 0.54 | | |
| 7.315 | 7.735 | 0.42 | 0.444 | 0.063 |

Since the plaque is 25 cm$^2$ in size: 17.76 mg/cm$^2$ for 2.52 standard deviation

SUMMARY

The inventive UV filter combination (formula 1) exhibits significantly less sand adhesion than the preparations containing no 2-phenylbenzimidazolesulfonic acid or ethylhexyl triazone.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic sunscreen composition, wherein the composition comprises a combination of
    (a) 4-(tert-butyl)-4'-methoxydibenzoylmethane,
    (b) 2,4,6-tris[anilino(p-carbo-2'-ethyl-1'-hexyloxy)]-1,3,5-triazine (INCI: Ethylhexyl Triazone),
    (c) 2,4-bis{[4-(2-ethylhexyloxy)-2-hydroxy]phenyl}-6-(4-methoxyphenyl)-1,3,5-triazine (INCI: Bis-Ethylhexyloxyphenol methoxyphenyl Triazine),
    (d) 2-phenylbenzimidazole-5-sulfonic acid and/or one or more salts of 2-phenylbenzimidazole-5-sulfonic acid,
    and wherein the composition contains no 2-hydroxy-4-methoxybenzophenone (INCI: Oxybenzone) and no ethylhexyl 2-cyano-3,3-diphenylacrylate (INCI: Octocrylene).

2. The composition of claim 1, wherein the composition further contains no 3-(4-methylbenzylidene)camphor.

3. The composition of claim 1, wherein the composition contains (c) and (d) in amounts which are effective for reducing the adhesion of sand on skin to which the composition has been applied.

4. The composition of claim 1, wherein the composition contains no titanium dioxide and no zinc oxide.

5. The composition of claim 1, wherein the composition is present as an O/W emulsion.

6. The composition of claim 1, wherein the composition comprises sodium stearoylglutamate as emulsifier.

7. The composition of claim 1, wherein the composition further comprises Silica Dimethyl Silylate.

8. The composition of claim 1, wherein the composition further comprises one or both of dibutyl adipate and dicaprylyl carbonate.

9. The composition of claim 1, wherein the composition further comprises one or more of alpha-lipoic acid, folic acid, phytoene, D-biotin, coenzyme Q10, alpha-glucosylrutin, carnitin, carnosin, natural and/or synthetic isoflavonoids, flavonoids, creatine, creatinine, taurine, β-alanine, dihydroxyacetone, 8-hexadecene-1,16-dicarboxylic acid, glycerylglucose, hyaluronic acid and/or salts thereof, licochalcone A.

10. The composition of claim 1, wherein the composition further comprises one or more of 1,2-hexanediol, 1,2-octanediol, 1,2-decanediol, 2-methyl-1,3-propanediol.

11. The composition of claim 10, wherein the composition comprises 2-methyl -1,3-propanediol.

12. The composition of claim 1, wherein the composition further comprises ethylhexylglycerol.

13. The composition of claim 1, wherein the composition further comprises xanthan gum.

14. The composition of claim 1, wherein the composition further comprises one or more of cetyl alcohol, stearyl alcohol, glyceryl stearate.

15. The composition of claim 1, wherein the composition is free from parabens, methylisothiazolinone, chloromethylisothiazolinone, and DMDM-hydantoin.

16. The composition of claim 1, wherein the composition comprises one or more fragrances selected from limonene, citral, linalool, alpha-isomethylionone, geraniol, citronellol, 2-isobutyl-4-hydroxy-4-methyltetrahydropyran, 2-tert-pentylcyclohexyl acetate, 3-methyl-5-phenyl-1-pentanol, 7-acetyl-1,1,3 ,4,4,6-hexamethyltetralin, adipic diester, alpha -amylcinnamaldehyde, alpha-methylionone, amyl C butylphenylmethylpropional cinnamal, amyl salicylate, amylcinnamyl alcohol, anise alcohol, benzoin, benzyl alcohol, benzyl benzoate, benzyl cinnamate, benzyl salicylate, bergamot oil, bitter orange oil, butylphenylmethylpropional, cardamom oil, cedrol, cinnamal, cinnamyl alcohol, citronellyl methylcrotonate, citrus oil, coumarin, diethyl succinate, ethyllinalool, eugenol, *Evernia furfuracea* extract, *Evernia prunastri* extract, farnesol, guaiacwood oil, hexylcinnamal, hexyl salicylate, hydroxycitronellal, lavender oil, lemon oil, linalyl acetate, mandarin oil, menthyl PCA, methyl heptenone, nutmeg oil, rosemary oil, sweet orange oil, terpineol, tonkabean oil, triethyl citrate, vanillin.

17. The composition of claim 1, wherein the composition has an SPF of at least 50.

18. The composition of claim 2, wherein the composition has an SPF of at least 50.

19. The composition of claim 3, wherein the composition has an SPF of at least 50.

20. The composition of claim 4, wherein the composition has an SPF of at least 50.

* * * * *